United States Patent
Hilfiker et al.

(10) Patent No.: US 8,901,296 B2
(45) Date of Patent: Dec. 2, 2014

(54) PROCESS FOR THE PREPARATION OF SUBSTANTIALLY PURE METHYLTHIONIUM CHLORIDE PENTAHYDRATE FORM A

(75) Inventors: Rolf Hilfiker, Basel (CH); Timo Rager, Basel (CH)

(73) Assignee: WisTa Laboratories Ltd., Singapore (SG)

( * ) Notice: Subject to any disclaimer, the term of this patent is extended or adjusted under 35 U.S.C. 154(b) by 0 days.

(21) Appl. No.: 13/497,691

(22) PCT Filed: Sep. 23, 2010

(86) PCT No.: PCT/IB2010/002543
§ 371 (c)(1),
(2), (4) Date: Mar. 22, 2012

(87) PCT Pub. No.: WO2011/036561
PCT Pub. Date: Mar. 31, 2011

(65) Prior Publication Data
US 2012/0289499 A1    Nov. 15, 2012

Related U.S. Application Data

(60) Provisional application No. 61/245,372, filed on Sep. 24, 2009.

(51) Int. Cl.
*C07D 279/18*    (2006.01)
(52) U.S. Cl.
CPC .................................. *C07D 279/18* (2013.01)
USPC ........................................................... 544/37
(58) Field of Classification Search
USPC .......................................... 544/37; 514/224.8
See application file for complete search history.

(56) References Cited

U.S. PATENT DOCUMENTS

2012/0238556 A1 *   9/2012   Hilfiker et al. .............   514/224.8

FOREIGN PATENT DOCUMENTS

| WO | WO 2006/032879 A2 | | 3/2006 |
|---|---|---|---|
| WO | WO 2006032879 A2 | * | 3/2006 |
| WO | WO 2007/110627 A2 | | 10/2007 |

OTHER PUBLICATIONS

J.O. Warwicker, Journal of the Chemical Society, 2531 (1955).*
H.E. Marr et al., 29 Acta Crystallographica Section B, 847-853 (1973).*
H.G. Brittain, Preparation and Identification of Polymorphs and Solvatemorphs, in Preformulation in Solid Dosage Form Development 185-228, 194 (Moji Christianah Adeyeye and Harry G. Brittain eds., 2008).*
J. Leonard et al., Advanced Practical Organic Chemistry 129-226 (2nd ed., 1985).*
Michael C. Pirrung, The Synthetic Organic Chemist's Companion (2006).*
S.R. Vippagunta et al., Advanced Drug Delivery Reviews, 48, 1 (2001).*
S.L. Morissette et al.,56 Advanced Drug Delivery Reviews, 275-300 (2004).*
J.K. Guillory, Generation of Polymorphs, Hydrates, Solvates, and Amorphous Solids, in Polymorphism in Pharmaceutical Solids 183-220 (H.G. Brittain ed., 1999).*
Rager, et al., "The crystalline state of methylene blue: a zoo of hydrates", *Physical Chemistry Chemical Physics*, 2012, doi.org/10.1039/c2cp40128B.
The International Search Report received in the parent International Application No. PCT/IB2010/002543, dated Mar. 25, 2011.
Budavari (Editor): "6137 Methylene Blue", Merck Index. Encyclopedia of Chemicals, Drugs, and Biologicals, Jan. 1996, p. 6142. (XP002628304).
Marr III, et al., "The crystal structure of methylene blue pentahydrate", Acta Crystallographica, Section B, vol. b29, No. 4, 1973, pp. 847-853.
Warwicker, "The Crystal Structure of Methylene-blue", Journal of the Chemical Society, Jan. 1955, p. 2531. (XP009143230).

* cited by examiner

*Primary Examiner* — James O. Wilson
*Assistant Examiner* — Alexander R Pagano
(74) *Attorney, Agent, or Firm* — Foley & Lardner LLP

(57) ABSTRACT

Substantially pure methylthioninium chloride pentahydrate form A is prepared from methylthioninium chloride by phase equilibration of suspensions, crystallization or solvent evaporation, whereby the water content of the solvent corresponds to a water activity of at least 0.4 at 25° C., and controlled drying of said methylthioninium chloride pentahydrate form A within its stability ranges of humidity, pressure and temperature.

7 Claims, No Drawings

PROCESS FOR THE PREPARATION OF SUBSTANTIALLY PURE METHYLTHIONIUM CHLORIDE PENTAHYDRATE FORM A

CROSS-REFERENCE TO RELATED PATENT APPLICATIONS

This application is the U.S. National Phase of PCT/IB2010/002543, filed Sep. 23, 2010, and which claims priority from U.S. Provisional Application No. 61/245,372, filed Sep. 24, 2009, all of which are incorporated herein by reference in entirety.

The present invention relates to a process for the preparation of substantially pure methylthioninium chloride pentahydrate Form A. The present invention also relates to the use of the so prepared Form A, preferably in pharmaceutical compositions.

Methylthioninium chloride (MTC) [Methylene Blue: 3,7-bisdimethylaminophenazothionium chloride, $C_{16}H_{18}ClN_3S$, 319.85 g/mol] was prepared for the first time in 1876 (*The Merck Index*, 13$^{th}$ edition, Merck & Co., Inc., 2001, entry 6085). Various synthesis methods are known and have recently been summarized in WO 2006/032879. This publication describes in example 16 a re-crystallization of MTC from a water solution by adding tetrahydrofuran and drying of the isolated solid at a temperature of 100° C., not suitable to avoid dehydration of MTC pentahydrate. WO 2006/032879 also states a number of applications of methylene blue, which include the use as a medical dye, as a redox indicator, an antiseptic, for the treatment and prevention of kidney stones, the treatment of melanoma, malaria, viral infections, and Alzheimer's disease. MTC has also been used as an oxidizing agent and as an antidote in the case of CO, nitrite and aniline poisoning.

MTC is known to exist in the form of hydrates. For example, the Fluka catalogue states in very general terms that MTC may contain up to 22% water [*Fluka Catalogue* 1997/1998, Fluka Chemie AG, 1997]. Structures with from one to five molecules of water have been formulated in the literature [J. O. Warwicker, *J. Chem. Soc.* (1955) 2531; G. F. Davidson, *J. Textile Institute* 38 (1947) T408-418]. The formation of a trihydrate has apparently found widespread acceptance [e.g. *The Merck Index*, 13$^{th}$ edition, Merck & Co., Inc., 2001, entry 6085]. However, this claim was already disputed more than 80 years ago, and the non-specific adsorption of water by MTC was proposed instead [H. Wales, O. A. Nelson, J. Am. Chem. Soc. 45 (1923) 1657; C. M. Martin, J. W. G. Neuhaus, F. H. Reuter, *Analyst* 71 (1946) 29-31].

To date, the only hydrate that has been characterized in detail is the pentahydrate of MTC [J. O. Warwicker, *J. Chem. Soc.* (1955) 2531; H. E. Marr III, J. M. Stewart, M. F. Chiu, *Acta Cryst.* B29 (1973) 847]. For this hydrate, even single crystal X-ray data are available. It consists of π-stacked columns of methylthioninium cations that are arranged in planes perpendicular to the α-axis of the crystal. The water molecules and chloride ions are located between these layers, whereby the chloride ions are concentrated in planes almost perpendicular to the water planes and parallel to the axis of the columns. The chloride ions are coordinated with three hydrogen bonds from 3/2 water molecules.

Presumably the same structure was earlier attributed to a tetrahydrate [W. H, Taylor, Z. Krist. 91 (1935) 450]. A phase transition between the pentahydrate and a second polymorphic form was described to occur near 30° C. in aqueous suspension [S. W. Bodman, S. P. Kodama, P. C. Pfeil, R. E. Stevens, J. Chem. Eng. Data 12 (1967) 500]. The second form was also obtained by vacuum drying of the pentahydrate at room temperature, and its water content was indicated to amount to approximately 1 mol/mol.

MTC is typically obtained by re-crystallization from aqueous solutions, whereby NaCl or HCl may be added to lower its solubility [W. H. Taylor, Z. Krist. 91 (1935) 450; J. O. Warwicker, *J. Chem. Soc.* (1955) 2531; H. E: Fierz-David, L. Blangey, *Fundamental Processes of Dye Chemistry*, Interscience, New York, 1949, p. 3111-314]. The product of the re-crystallization contains noticeable amounts of excess water, which requires a subsequent drying step. Investigations have shown that it is difficult to obtain a product of well defined stoichiometry, such as a pure MTC pentahydrate Form A, by this purification process.

The thermodynamic stability of hydrates is always a function of temperature and relative humidity. Exposing a hydrate to temperature and relative humidity conditions outside its stability domain may result in its transformation into other forms.

The solid state form of a compound is of great importance for pharmaceutical applications. It may influence the chemical and physical stability of the compound itself and of its formulations, or may have an impact on pharmacokinetics and bioavailability. In the case of hydrates, the composition has also an influence on the correct dosage of the active pharmaceutical ingredient.

The present invention provides a safe and reproducible process for the preparation of substantially pure methylthioninium chloride pentahydrate Form A, which can be applied in an industrial manufacture. The present invention further provides a process, which results in a Form A content of at least 95% by weight, preferably at least 98%, most preferred at least 99% based on the total weight of methylthioninium chloride. The present invention also provides a storage stable methylthioninium chloride which is substantially pure methylthioninium chloride pentahydrate Form A and which can be easily metered for a defined content in pharmaceutical compositions. The present invention also provides a storage stable methylthioninium chloride having a Form A content of at least 95% by weight, preferably at least 98%, most preferred at least 99% based on the total weight of methylthioninium chloride.

The present inventors have found that the use of organic solvents and humidity control during crystallization treatments lead to the formation of MTC pentahydrate Form A, which can be easier dried and simultaneously maintains MTC pentahydrate form A under stability conditions of MTC pentahydrate Form A.

A first aspect of the invention is a process for the preparation of substantially pure methylthioninium chloride pentahydrate Form A, wherein a) methylthioninium chloride is suspended in an organic solvent with a water content corresponding to a water activity of at least 0.4 at 25° C., the suspension is kept at low temperature, and the solid is isolated and dried to remove the organic solvent and any excess water from the solid;

b) methylthioninium chloride is dissolved at elevated temperatures in an organic solvent with a water content corresponding to a water activity of at least 0.4 at 25° C., the solution is cooled, the precipitated solid is isolated and dried to remove the solvent and any excess water from the solid; or c) methylthioninium chloride is dissolved in an organic solvent with a water content corresponding to a water activity of at least 0.4 at 25° C., and the solvent and any excess water is evaporated to dryness of the solid.

"Substantially pure" as used above refers to methylthionium chloride having a Form A content of at least 95% by weight, preferably at least 98%, most preferred at least 99% based on the total weight of methylthioninium chloride.

Methylthioninium chloride may as starting material consist of a water-free or a water containing MTC comprising e.g. from 0.1 to 22 percent by weight of water, based on the total weight of the starting material. Methylthioninium chloride may be in the form of a hydrate or an arbitrary mixture of hydrates. MTC as prepared according to WO 2006/032879 may be used (e.g. example 17). It is advantageous to know the total water content of the starting material so that it can be taken into account for the calculation of the water activity in the solvent composition. The water content can be determined by thermogravimetry or Karl Fischer titration.

The progress of the conversion may be followed by appropriate analytical methods such as thermogravimetry, differential scanning calorimetry, infrared spectroscopy or X-ray powder diffraction. A particularly suitable method is X-ray powder diffraction, which provides characteristic signals for MTC pentahydrate Form A independently of the presence of residual organic solvent.

The organic solvent, which includes a mixture of at least two organic solvents, preferably possesses a poor solubility for MTC pentahydrate Form A at the temperature of isolation of the crystalline product, which is typically at room temperature or below. Solubility for MTC pentahydrate Form A is influenced by increased temperature and/or presence of water. A solubility of less than 20 g/l and in particular less than 2 g/l at room temperature is preferred for process variants a) and b). The organic solvent is preferably miscible with water. The vapor pressure of the organic solvent preferably exceeds the one of water. Particularly suitable solvents include methanol, ethanol, 1-propanol, 2-propanol, 2-methyl-2-propanol, acetonitrile, tetrahydrofurane, 1,4-dioxane and acetone and mixtures thereof. Particularly preferred solvents for process variants a) and b) include 1-propanol, tetrahydrofurane and acetone and mixtures thereof. Particularly preferred solvents for process variant c) include methanol and ethanol and mixtures thereof.

The water content is chosen in such a way that the thermodynamic stability of MTC pentahydrate Form A is given up to the end of the process. The necessary minimum water activity in solution for thermodynamic stability can be determined experimentally, for example by determining the water content of a solution that is in equilibrium with a mixture of methylthioninium pentahydrate Form A and the hydrate that is thermodynamically stable at lower water activity. For this purpose, the composition of a water/solvent mixture of a suspension of methylthioninium pentahydrate Form A may be changed until a mixture of the two polymorphic forms in question is detected in the solid. The water content in solution may then be determined e.g. by Karl-Fischer titration. Based on such an experiment, at 25° C., thermodynamic stability of MTC pentahydrate Form A is given for a water activity of 0.4 or higher, i.e. up to 1.0 [corresponding to at least 40% and up to 100% relative humidity (r.h.)]. A water content of 5 wt.-% in 2-propanol, at 25° C., is required to achieve the minimum water activity of 0.4. The necessary water activity decreases with decreasing temperature and increases with increasing temperature. Different water contents are required for other organic solvents in order to achieve the same minimum water activity of 0.4. The values can be taken from the literature (e.g. D. R. Lide, H. V. Kehiaian, CRC handbook of thermophysical and thermochemical data, CRC press, Boca Raton, 1994; J. Gmehling, U. Onken, W. Arlt, P. Grenzheuser, U. Weidlich, B. Kolbe, J. Rarey-Nies, Vapor-Liquid Equilibrium Data Collection, DECHEMA, Frankfurt/M., 1978-1992).

Apart from this, the water content is preferably chosen in such a way that complete solubility of MTC pentahydrate Form A is achieved at the maximum temperature of the crystallization step and a sufficiently low solubility is given at the minimum temperature of the crystallization step in order to ensure high yields of MTC pentahydrate Form A. The water content of the liquid phase preferably does not exceed 50 wt.-%, based on the liquid phase, more preferably does not exceed 20 wt.-%, and most preferably does not exceed 10 wt.-%.

Low temperature in process variant a) may mean in the context of the invention a temperature range from 0 to 35° C. and more preferably 10 to 30° C. Temperature cycles within this temperature range may be applied during this phase equilibration process.

The phase equilibration process a) and the crystallization processes b) and c) may be carried out under stirring. Dissolution of the starting material in process variant b) may be carried out under heating up to the reflux temperature of the solvent, preferably to 40 to 100° C., which means in the context of the invention elevated temperature. Cooling of the hot solution may be carried out continuously or in steps. Seeding with nucleating agents such as MTC Form A crystals may be advantageous.

The suspension according to process variant a) has to be equilibrated for sufficiently long time to insure complete conversion. Amongst other parameters, the required time will depend on the solids content, particle size, temperature and water concentration. Typically, an equilibration time of from hours to several days is sufficient. The progress of the conversion may be followed as described before.

The organic solvent or solvent mixture used in process variant c) has to have a reasonably high dissolving power for the starting material, either by itself or in combination with water. The solubility of MTC pentahydrate Form A is preferably higher than 20 g/l at room temperature, especially preferred higher than 50 g/l, and most preferred higher than 100 g/l. The vapor pressure of the organic solvent or solvent mixture preferably exceeds the one of water.

Process variant c) according to the invention preferably uses starting materials which already have an appropriate chemical purity, since no purification is involved in this process c) contrary to re-crystallization (process variant b) or phase equilibration (process variant a). Water activity in process variant c) may either be provided as water in the liquid phase or by evaporation at sufficiently high relative humidity. The required water activity in solution or the relative humidity of the gas phase is given by the thermodynamic stability limits of MTC pentahydrate form A. This stability limit amounts to about at least 40% r.h. at 25° C. and increases to higher values at higher temperatures. According to the present invention, a temperature close to room temperature is preferred for the evaporation process in order to have a broad stability window of MTC pentahydrate Form A available.

Evaporation of solvent according to process variant c) is preferably carried out at low temperature such as 10 to 30° C. and a relative humidity of preferably 40 to 80%. In one embodiment, the solution is stored under ambient conditions to let slowly evaporate the solvent. A humidified inert gas flow such as a nitrogen or noble gas flow may be applied to accelerate solvent evaporation.

The starting amount of methylthioninium chloride hydrates in the process variants a), b) or c) according to the invention may range from 0.1 to 60% by weight, preferably 1 to 50% by weight and more preferably 5 to 40% by weight, based on the total weight of the suspension or solution.

Isolation of the solid MTC pentahydrate Form A is typically achieved by decantation and preferably by filtration.

Drying of said methylthioninium chloride pentahydrate Form A must be controlled within its stability ranges of humidity, vacuum and temperature.

Drying is intended for the selective removal of excess water and especially solvent. It may be performed by either passing a humidified gas flow over the sample or by vacuum drying, The required relative humidity of the gas flow and the appropriate minimum pressure for vacuum drying depend on the temperature and may be estimated from dynamic vapor sorption experiments. In this type of experiment, the sample under investigation is exposed to a humidified gas flow with a steadily changing relative humidity at constant temperature. The weight of the sample is determined at short time intervals, which permits to detect a change in the hydration state. Dynamic vapor sorption curves give an approximate indication of the kinetic stability domain of a hydrate. According to such measurements, MTC pentahydrate Form A is kinetically stable down to approximately 15% relative humidity at 25° C. and approximately 30% relative humidity at 40° C. These values constitute the lower limits of relative humidity that should not be undercut. Taking into account the vapor pressure of water at these temperatures (e.g. D. R. Lide, *CRC handbook of chemistry and physics*, $80^{th}$ edition, CRC press, Boca Raton, 1999, p. 6-10), these relative humidity values translate into pressures of approximately 5 mbar and 20 mbar, respectively, that should not be undercut at these temperatures. According to the present invention, a temperature close or even below room temperature is generally preferred in order to have a large stability domain of the pentahydrate available. In principle, no upper limit is given to the relative humidity and the applied pressure, respectively. However, the risk of water condensation in combination with deliquescence and unacceptably long drying times may result.

Preferred conditions to carry out the process variants according to the invention are: isolation of the product at a temperature not higher than 40° C., preferably not higher than 30° C., and most preferred not higher than 25° C.; removal of excess solvent and excess water by vacuum drying or in a flow of humid inert gas; performing vacuum drying at a temperature not higher than 40° C. and a pressure not lower than 20 mbar, preferably at a temperature not higher than 25° C. and a pressure not lower than 5 mbar; performing drying with an inert gas flow at a temperature not higher than 40° C. and at a relative humidity of the gas not below 30%, preferably at a temperature not higher than 25° C. and at a relative humidity of the gas not below 15%.

Substantially pure Methylthioninium chloride pentahydrate Form A is obtained in high yields and good crystallinity. The kinetic and thermodynamic stability of substantially pure Form A provides easy and safe handling and processing under the described stability conditions without conversion to other crystalline forms or dehydration, ensuring preparation of storage stable, well dosed compositions, preferably pharmaceutical formulations, In particular, Form A is thought to be stable at high relative humidity down to about 35% r.h. or 40% r.h. Form A is also stable at 25° C.

A further aspect of the present invention relates to the drying of MTC pentahydrate Form A to remove excess water and/or solvent either by vacuum drying or by drying in a flow of humid insert gas, such as nitrogen. The conditions should be such that the MTC pentahydrate form A is not dehydrated.

This drying should be carried out a temperature not higher than 40° C. Preferably the drying is carried out a temperature not higher than 30° C. or even 25° C.

If the drying is carried out by vacuum drying, the vacuum should be greater than or equal to 60 mbar.

If the drying is carried out in a flow of humid insert gas, the relative humidity of the gas should be adjusted so as not to dehydrate the MTC pentahydrate form A. In some embodiments, the relative humidity should not be below 30%. However, in further embodiments, whilst if the drying is carried out at 40° C., the relative humidity of the gas should not below 30%, if the drying is carried out at 25° C., then the relative humidity of the gas can be lower, but should not below 15%.

A further aspect of the present invention provides substantially pure methylthioninium chloride pentahydrate Form A which is obtained by, or is obtainable by, the methods described above.

Compositions

One aspect of the present invention pertains to compositions comprising substantially pure MTC pentahydrate Form A which is obtained by, or is obtainable by, a method as described herein.

In one embodiment, the composition further comprises a pharmaceutically acceptable carrier, diluent, or excipient.

Methods of Inactivating Pathogens

One aspect of the present invention pertains to use of substantially pure MTC pentahydrate Form A, which is obtained by, or is obtainable by, a method as described herein, in a method of inactivating a pathogen in a sample (for example a blood or plasma sample), the method comprising introducing the compound into the sample, and exposing the sample to light.

Methods of Medical Treatment

One aspect of the present invention pertains to substantially pure MTC pentahydrate Form A, which is obtained by, or is obtainable by, a method as described herein, for use in a method of treatment (e.g., of a disease condition) of the human or animal body by therapy.

One aspect of the present invention pertains to use of substantially pure MTC pentahydrate Form A, which is obtained by, or is obtainable by, a method as described herein, for the manufacture of a medicament for use in the treatment of a disease condition.

One aspect of the present invention pertains to use of substantially pure MTC pentahydrate Form A, which is obtained by, or is obtainable by, a method as described herein, in the treatment of a disease condition.

One aspect of the present invention pertains to a method of treatment of a disease condition in a patient, comprising administering to said patient a therapeutically-effective amount of substantially pure MTC pentahydrate Form A, which is obtained by, or is obtainable by, a method as described herein.

Disease Conditions

In one embodiment, the disease condition is a tauopathy.

A "tauopathy" is a condition in which tau protein (and aberrant function or processing thereof) plays a role. Alzheimer's Disease is an example of a tauopathy. The pathogenesis of neurodegenerative disorders such as Pick's disease and Progressive Supranuclear Palsy (PSP) appears to correlate with an accumulation of pathological truncated tau aggregates in the dentate gyrus and stellate pyramidal cells of the neocortex, respectively. Other dementias include frontotemporal dementia (FTD); parkinsonism linked to chromosome 17 (FTDP-17); disinhibition-dementia-parkinsonism-amyotrophy complex (DDPAC); pallido-ponto-nig ral degeneration (PPND); Guam-ALS syndrome; pallido-nigro-luysian degeneration (PNLD); cortico-basal degeneration (CBD) and others (see, e.g., Wischik, C. M., Theuring, F. & Harrington, C. R. (2000) The molecular basis of tau protein pathology in Alzheimer's disease and related neurodegenerative dementias. In Neurobiology of Alzheimer's Disease (Eds. D. Dawbarn & S. J. Allen) Oxford University Press, Oxford, 103-206, especially Table 5.1 therein). Each of these diseases, which is characterized primarily or partially by abnormal tau aggregation, is referred to herein as a "tauopathy."

In one embodiment, the disease condition is Alzheimer's disease (AD).

In one embodiment, the disease condition is skin cancer.

In one embodiment, the disease condition is melanoma.

In one embodiment, the disease condition is viral, bacterial or protozoal.

In one embodiment, the protozoal disease condition is malaria. In this embodiment treatment may be in combination with another antimicrobial agent e.g. in combination with chloroquine or atovaquone.

In one embodiment, the viral disease condition is caused by Hepatitis C, HIV or West Nile virus.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously.

Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Routes of Administration

Substantially pure MTC pentahydrate Form A, or pharmaceutical composition comprising it, may be administered to a subject/patient by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal (including, e.g., intracatheter injection into the brain); by implant of a depot or reservoir, for example, subcutaneously or intramuscularly.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for substantially pure MTC pentahydrate Form A to be used (e.g., administered) alone, it is often preferable to present it as a composition or formulation.

In one embodiment, the composition is a pharmaceutical composition (e.g., formulation, preparation, medicament) comprising substantially pure MTC pentahydrate Form A, as described herein, and a pharmaceutically acceptable carrier, diluent, or excipient.

In one embodiment, the composition is a pharmaceutical composition comprising at least substantially pure MTC pentahydrate Form A, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, Handbook of Pharmaceutical Additives, 2nd Edition (eds. M. Ash and I. Ash), 2001 (Synapse Information Resources, Inc., Endicott, New York, USA), Remington's Pharmaceutical Sciences, 20th edition, pub. Lippincott, Williams & Wilkins, 2000; and Handbook of Pharmaceutical Excipients, 2nd edition, 1994.

Another aspect of the present invention pertains to methods of making a pharmaceutical composition comprising admixing substantially pure [$^{11}$C]-radiolabelled MTC pentahydrate Form A, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Examples of Preferred Formulations

One aspect of the present invention pertains to a dosage unit (e.g., a pharmaceutical tablet or capsule) comprising 20 to 300 mg of substantially pure MTC pentahydrate form A obtained by, or obtainable by, a process as described herein and a pharmaceutically acceptable carrier, diluent, or excipient.

In one embodiment, the dosage unit is a tablet.
In one embodiment, the dosage unit is a capsule.
In one embodiment, the amount is 20 to 200 mg.
In one embodiment, the amount is about 20 mg.
In one embodiment, the amount is about 60 mg.
In one embodiment, the amount is about 100 mg.
In one embodiment, the amount is about 150 mg.
In one embodiment, the amount is about 200 mg.
In one embodiment, the pharmaceutically acceptable carrier, diluent, or excipient is or comprises one or both of a glyceride (e.g., Gelucire 44/14®; lauroyl macrogol-32 glycerides PhEur, USP) and colloidal silicon dioxide (e.g., 2% Aerosil 200®; Colliodal Silicon Dioxide PhEur, USP).

Dosage

It will be appreciated by one of skill in the art that appropriate dosages of substantially pure MTC pentahydrate form A, and compositions comprising substantially pure MTC pentahydrate form A, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of substantially pure MTC pentahydrate form A is in the range of about 100 ng to about 25 mg (more typically about 1 µg to about 10 mg) per kilogram body weight of the subject per day.

In one embodiment, substantially pure MTC pentahydrate form A is administered to a human patient according to the following dosage regime: about 100 mg, 3 times daily.

In one embodiment, substantially pure MTC pentahydrate form A is administered to a human patient according to the following dosage regime: about 150 mg, 2 times daily.

In one embodiment, substantially pure MTC pentahydrate form A is administered to a human patient according to the following dosage regime: about 200 mg, 2 times daily.

Unless otherwise specified room temperature corresponds to 25° C. and ambient conditions correspond to room temperature and a pressure of 1,013 bar.

The following examples explain the invention in more detail. Starting materials are prepared according to examples described in WO 2006/032879 having various water contents corresponding to a lower water content than methylthioninium chloride pentahydrate.

Powder X-ray Diffraction (PXRD) is performed on a Bruker D8 Advance powder X-ray diffractometer using CuKα radiation. D-spacings are calculated from the 2θ values using the wavelength of 1.54180 Å. Generally, 2θ values are within an error of ±0.1-0.2°. The experimental error on the d-spacing values is therefore dependent on the peak location.

The characteristic peaks in 2θ with the corresponding d-values (Å) are given in Table 1 for Methylthioninium chloride pentahydrate form A.

TABLE 1 d-Spacings for crystal form A

| Angle [° 2θ] | d-spacing [Å] | Intensity (qualitative) |
|---|---|---|
| 5.7 | 15.5 | vs |
| 9.2 | 9.6 | vs |
| 9.6 | 9.2 | vs |
| 10.8 | 8.2 | s |
| 11.3 | 7.8 | m |
| 18.7 | 4.75 | vs |
| 19.3 | 4.60 | s |
| 20.4 | 4.35 | m |
| 21.7 | 4.10 | m |
| 21.9 | 4.06 | m |
| 24.6 | 3.62 | m |
| 25.6 | 3.48 | vs |
| 26.0 | 3.43 | s |
| 26.2 | 3.40 | vs |
| 26.4 | 3.38 | vs |
| 27.3 | 3.27 | s |
| 28.0 | 3.19 | s |
| 28.4 | 3.14 | s |
| 29.2 | 3.06 | m |

The abbreviations in brackets mean: (vs)=very strong intensity; (s)=strong intensity; (m)=medium intensity; and (w)=weak intensity.

Methylthioninium chloride pentahydrate form A exhibits the following characteristic 2θ values (±0.1°): 5.7, 9.2, 9.6, 18.7, 25.6, 26.2 and 26.4.

Methylthioninium chloride pentahydrate form A preferably exhibits the following characteristic a values)(±0.1°): 5.7, 9.2, 9.6, 10.8, 18.7, 19.3, 25.6, 26.0, 26.2, 26.4, 27.3, 28.0 and 28.4.

Methylthioninium chloride pentahydrate form A most preferably exhibits the following characteristic 2θ values (±0.1°): 5.7, 9.2, 9.6, 10.8, 11.3, 18.7, 19.3, 20.4, 21.7, 21.9, 24.6, 25.6, 26.0, 26.2, 26.4, 27.3, 28.0, 28.4 and 29.2.

EXAMPLES

Example 1

A suspension of 181 mg of a mixture containing methylthioninium chloride hydrates in 2 ml acetone/water (1:1) was stirred at room temperature for 4 days. The solid was filtered off and dried at room temperature and 5 to 10 mbar for 15 minutes. 150 mg of pure MTC pentahydrate Form A are obtained as confirmed by X-ray powder diffraction.

Example 2

100 mg of a mixture of methylthioninium chloride hydrates were suspended in 2 ml 2-propanol and 0.1 ml water (corresponding to approximately 46% relative humidity). The suspension is stirred at room temperature for 6 days. The solid was filtered off and dried at room temperature and 5 to 10 mbar for 5 minutes. A sample of pure MTC pentahydrate Form A is obtained as confirmed by X-ray powder diffraction.

Example 3

113 mg of methylthioninium chloride Form A were dissolved in 6 ml boiling tetrahydrofurane/water 2:1. Long needles crystallize upon cooling back to room temperature. They were filtered off and dried at ambient condition. X-ray powder diffraction confirms pure MTC pentahydrate Form A.

Example 4

103 mg of methylthioninium chloride Form A were dissolved in 5 ml boiling 2-propanol and water (4:1). Crystallization starts soon after cooling back to room temperature. The solid was filtered off and dried at ambient condition. X-ray powder diffraction confirms pure MTC pentahydrate Form A.

Example 5

105 mg of a mixture of methylthioninium chloride hydrates were dissolved in 2 ml methanol. The solution was filtered through a 0.2 µm syringe filter and left in an open glass vial for evaporation to dryness at ambient conditions with a relative humidity above 40%. X-ray powder diffraction confirms pure MTC pentahydrate Form A in the residue.

Example 6

100 mg of a mixture of methylthioninium chloride hydrates were dissolved in 3 ml methanol/water (2:1). The solution was filtered through a 0.2 µm syringe filter and left in an open glass vial for evaporation at ambient conditions with a relative humidity above 40%. X-ray powder diffraction confirms pure MTC pentahydrate Form A in the residue.

Example 7

106 mg of a mixture of methylthioninium chloride hydrates were dissolved in 2 ml methanol/ethanol (1:1). The solution was filtered through a 0.2 µm syringe filter and left in an open glass vial for evaporation at ambient conditions with a relative humidity above 40%. X-ray powder diffraction confirms pure MTC pentahydrate Form A in the residue.

Example 8

101 mg of a mixture of methylthioninium chloride hydrates were dissolved in 2 ml methanol/2-propanol (1:1). The solution was filtered through a 0.2 µm syringe filter and left in an open glass vial for evaporation at ambient conditions with a relative humidity above 40%. X-ray powder diffraction confirms pure MTC pentahydrate Form A in the residue.

Example 9

130 mg of a mixture of methylthioninium chloride hydrates were dissolved in 1 ml methanol. The solution was filtered through a 0.2 µm syringe filter and added to 10 mL acetonitrile. No precipitation occurs, and the solution is left for evaporation in an open glass vial at ambient conditions with a relative humidity above 40%. X-ray powder diffraction confirms pure MTC pentahydrate form A in the residue.

Example 10

130 mg of a mixture of methylthioninium chloride hydrates were dissolved in 1 ml methanol. The solution was filtered through a 0.2 syringe filter and added to 10 ml 2-propanol. No precipitation occurs, and the solution is left for evaporation at ambient conditions with a relative humidity above 40%. X-ray powder diffraction confirms pure MTC pentahydrate form A in the residue.

The invention claimed is:

1. A method of drying of methylthioninium chloride pentahydrate Form A to remove excess water and/or solvent by drying in a flow of humid nitrogen or a humid noble gas, wherein the excess water and/or solvent is removed, and the dried methylthioninium chloride pentahydrate Form A has a Form A content of at least 95% based on the total weight of methylthioninium chloride.

2. A method according to claim 1, wherein the drying is carried out at a temperature not higher than 40° C.

3. A method according to claim 2, wherein the drying is carried out at a temperature not higher than 30° C.

4. A method according to claim 3, wherein the drying is carried out at a temperature not higher than 25° C.

5. A method according to claim 1, wherein the relative humidity of the nitrogen or the noble gas is not below 30%.

6. The method of claim 1, wherein the dried methylthioninium chloride pentahydrate Form A has a Form A content of at least 98% based on the total weight of methylthioninium chloride.

7. The method of claim 1, wherein the dried methylthioninium chloride pentahydrate Form A has a Form A content of at least 99% based on the total weight of methylthioninium chloride.

* * * * *